(12) United States Patent
Hoffman et al.

(10) Patent No.: US 7,124,031 B1
(45) Date of Patent: Oct. 17, 2006

(54) SYSTEM FOR MONITORING REGULATION OF PHARMACEUTICALS FROM DATA STRUCTURE OF MEDICAL AND LABORTORY RECORDS

(75) Inventors: Peter F. Hoffman, Round Hill, VA (US); Monique Parr, North Potomac, MD (US); Aida A. Leroy, Westfield, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

(21) Appl. No.: 09/569,213

(22) Filed: May 11, 2000
(Under 37 CFR 1.47)

(51) Int. Cl.
*G01N 33/48* (2006.01)
*G01N 31/00* (2006.01)
*G06F 7/00* (2006.01)

(52) U.S. Cl. .............................. 702/19; 707/1; 702/22
(58) Field of Classification Search .................... 705/3; 814/3; 702/19, 22; 701/1
See application file for complete search history.

(56) References Cited

U.S. PATENT DOCUMENTS 5,487,384 A * 1/1996 Lee ............................. 600/316
5,743,250 A * 4/1998 Gonda et al. ........... 128/200.14
5,845,255 A * 12/1998 Mayaud ......................... 705/3

OTHER PUBLICATIONS

Wolf et al., Comprehensive Psychiatry, vol. 30, No. 6, 1989, pp. 534-545.*
Hansen et al. Journal of Clinical Psychiatry, vol. 49, No. 4, 1988, pp. 139-141.*
Leslie et al., Am J Psychiatry, vol. 156, No. 8, 1999, pp. 1250-1257.*
Alberts et al., Molecular Biology of the Cell, Third Edition, Garland Publishing, pp. 1-20, 1994.*
Koide et al., International Journal of Medical Informatics, vol. 57, pp. 11-19, Jan. 2000.*
Tierney et al., JAMA, vol. 259, pp. 1194-1198, 1988.*
Gonzalez et al., Am. J. Emerg. Med., vol. 7, 395-401, 1989.*
McMullin et al., Arch Intern Med, vol. 159, pp. 2077-2082, Sep. 1999.*

* cited by examiner

*Primary Examiner*—Tim Vo
*Assistant Examiner*—Cheyne D. Ly
(74) *Attorney, Agent, or Firm*—Irah H. Donner, Esq.; Wilmer Cutler Pickering Hale and Dorr LLP

(57) ABSTRACT

A system is provided that integrates of records of clinical laboratory services into the assessment and optimization of patient health care and, in particular, regulation of the use of pharmaceuticals. Laboratory test result records are used in conjunction with other health care benefits records to monitor regulation of use of pharmaceuticals by patients. The incorporation of laboratory tests and results into such a utilization system allows improvement in the management of a patient's therapy based on a more precise picture of the patient's level of illness as revealed by the laboratory test results. The system of the present invention also allows optimization of the selection of laboratory tests to be performed, and also provides an outcome assessment of the risk of hospitalization due to pharmaceutical treatments resulting in physician intervention, leading to a change in physician prescribing behavior and, accordingly, a decrease in drug induced hospitalizations and improved quality of patient care and savings of health care costs.

30 Claims, 9 Drawing Sheets

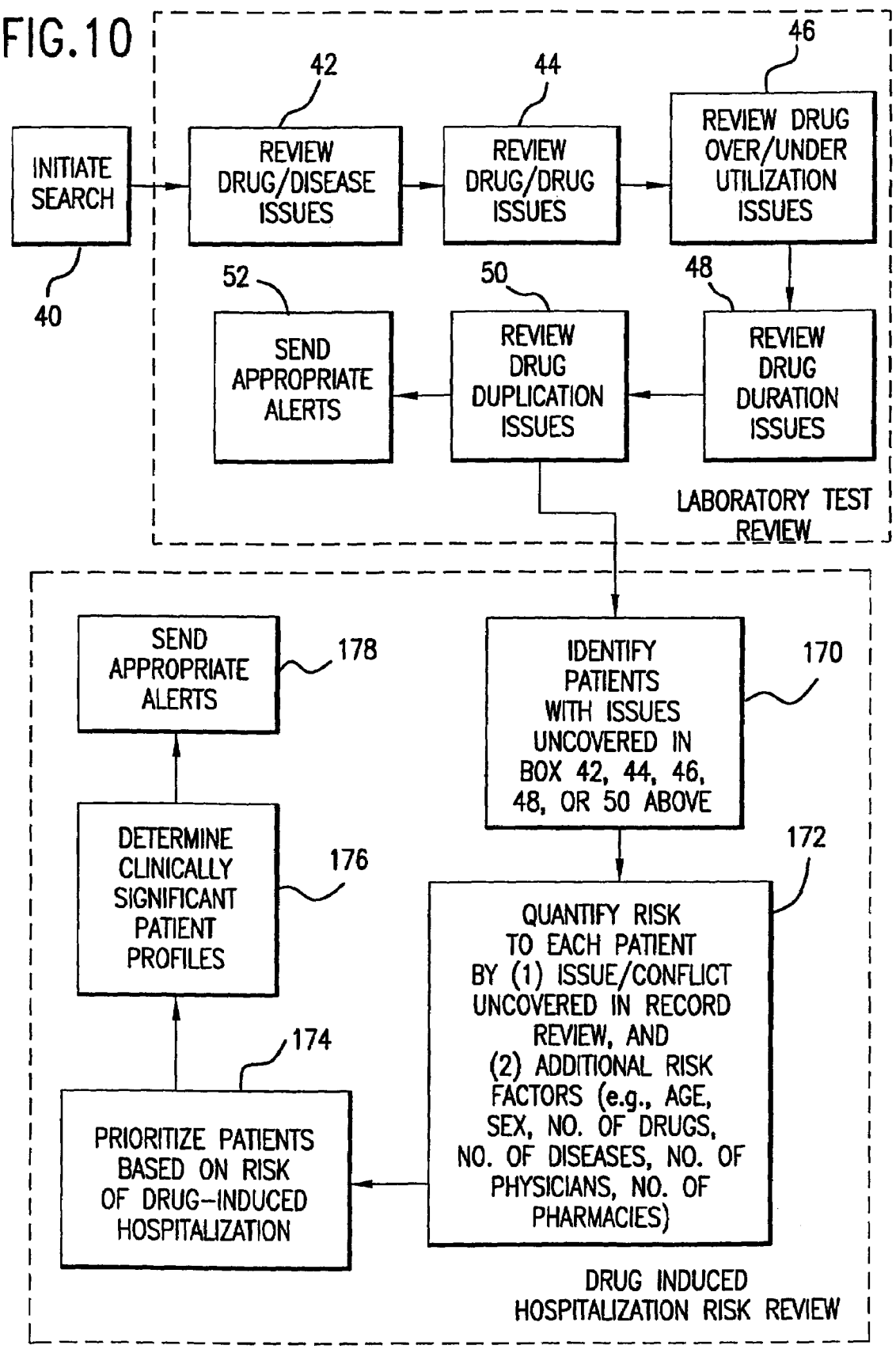

SYSTEM FOR MONITORING REGULATION OF PHARMACEUTICALS FROM DATA STRUCTURE OF MEDICAL AND LABORTORY RECORDS

BACKGROUND OF THE INVENTION

The present invention relates to a system that provides an integration of records of clinical laboratory services into the assessment and optimization of patient health care and, in particular, use of pharmaceuticals. The laboratory records are used in conjunction with other health care benefits records to monitor regulation of use of pharmaceuticals by patients.

Laboratory results provide quantitative and continuous measures of a patient's physical status. Optimal management of many diseases, especially those treated with pharmaceuticals, requires routine monitoring for blood levels of drugs or key disease indicators. The incorporation of laboratory results into a system to monitor regulation of drug use provides a better understanding of the relationship between medical services, prescribed drugs, and laboratory findings.

Current drug utilization review software uses the appearance and number of ICD9CM diagnosis codes reported on health care claims to assume illness and severity of illness. In using ICD9CM and drug data alone, disease management relies heavily on limited surrogate measures of disease progression and outcomes. The presence of health benefit claims records for drugs to treat diseases is also used as a proxy of illness. Using these two data elements (ICD9CM diagnosis codes and NDC drug codes), one commercially available software package, known as RationalMed(TM), applies rules to identify inappropriate drug therapy. These types of inappropriate drug therapy are categorized as drug-disease problems, drug—drug problems, drug utilization problems, over/under utilization of drugs, drug duration problems, and drug duplication problems. The presently available software system does not use or incorporate laboratory tests and their results into the drug monitoring function.

Laboratory result data support the monitoring of clinical outcomes (positive or negative) of important and sometimes costly drug therapies based on the longitudinal tracking of laboratory result indicators. Laboratory test results also enable the monitoring of blood levels of certain medications. By combining actual blood level results with over and under dosing criteria into drug utilization review software, frequent false positive findings that occur by using apparent daily dose alone may be minimized. And, as drug—drug interaction screening has proven to be an important clinical tool, similarly, inclusion of drug-laboratory interactions in drug utilization software would furnish treatment providers with information on potentially dangerous drug interactions that could lead to erroneous treatment decisions. Almost universally, the addition of laboratory test values to drug utilization software will provide sensitive continuous measures to support and validate assumptions drawn from the categorical data routinely available from medical claims data.

SUMMARY OF THE INVENTION

The present invention involves the incorporation of laboratory tests and results into drug utilization review software and provides a system for monitoring the utilization of drugs and pharmaceuticals. The incorporation of laboratory tests and results into such a utilization system allows improvement in the management of a patient's therapy based on a more precise picture of the patient's level of illness as revealed by the laboratory test results. The system of the present invention also allows optimization of the selection of laboratory tests to be performed, that is, it provides a review of laboratory utilization. The system of the present invention also provides an outcome assessment of the risk of hospitalization due to pharmaceutical treatments.

The system of the present invention is aimed at alerting the providers of health care to opportunities for improved management of patient care. By evaluating information relating to drugs, diseases and laboratory results, the system alerts providers to the potential for false positive or false negative results caused by the presence of a confounding drug or disease condition. The system also alerts providers if a laboratory value is not in the normal range and the patient's disease is not improving. For example, the system can alert providers with regard to uric acid, potassium, or levothyroxine levels. Similarly, the system can alert the provider to whether potential side effects are developing, such as with regard to warfarin, clozaril or zidovudine. Laboratory results in the normal range will indicate positive outcomes.

The system is also designed to alert providers to the lack of appropriate monitoring when required for a patient with a specific condition or particular drug. When patients are initially placed on a therapy they are monitored by the system every X days for Z duration. A change to maintenance therapy requires or causes a change in the schedule for monitoring.

Alerts are also provided by the system to the provider to monitor for drug levels or laboratory values if the initiation or discontinuation of a drug affects the levels of another drug. An alert will also occur if the value of an initial test requires the use of a subsequent different test. For example, if a screening test is positive, a more specific test may be needed or indicated. Alerts are also provided by the system if a laboratory value is not in the therapeutic range. Thus, the provider will be warned if the patient's drug level is toxic or ineffective, such as in the use of theophylline, phenytoin, carbamazepine, lithium or digoxin.

The system of the present invention is also designed to provide optimization of the selection of laboratory tests or a review of laboratory utilization. Such a review may result in either an increase or decrease in the number of tests, but in most circumstances will result in a decrease in the number of tests ordered.

For example, the system will monitor for tests that should be performed at predetermined frequencies and not more or less than the recommended frequency. Repetitive tests with no change in value are wasteful. Conversely, not repeating a test when therapy has been instituted to determine the effect of the therapy may result in the prolonged use of an ineffective therapy. Also, certain conditions require frequent monitoring.

In other circumstances, certain tests may be invalidated or rendered useless under certain conditions. For example, a serum ferritin level is useless in an alcoholic individual because ferritin is released from a damaged liver. Similarly, tests that are no longer used as the preferred or "state of the art" tests can be indicated and removed from the laboratory protocol. Other tests that are considered unreliable because they have limited specificity, sensitivity, high variability or the like can also be indicated by the present system and eliminated from use. Finally, tests that measure the same functional area and provide duplicative information can also be eliminated.

Another objective of the system of the present invention is to provide a research tool that incorporates laboratory test results data into a longitudinal, patient-specific medical and pharmaceutical history database, i.e., a continuous patient record across time. The cost benefit assessment of new drugs includes measuring the attainment of a treatment goal in relation to the costs of treatment with the drug. The costs associated with drug treatment are considered to be those costs of the treatment itself, the services required for monitoring the illness and the therapy, and the cost of treating the side effects of the therapy. For many illnesses, the treatment goal (prevention of heart attacks, strokes, kidney damage) will not be determined until far into the future. Thus, in order to attribute a benefit to a drug, interim outcome measures would contribute to the assessment of attaining a treatment goal (i.e., lowering of blood pressure, or cholesterol). Some examples of drug therapy and a laboratory result indicator assisting in defining beneficial outcomes are the following:

(1) antiviral drugs and CD4 levels;
(2) cholesterol lowering drugs and cholesterol levels;
(3) anti-diabetic drugs and hemoglobin A1C levels;
(4) anti-bacterial drugs and culture results;
(5) thyroid hormones and thyroid levels; and
(6) anti-coagulants and blood clotting values.

The present invention is also directed to solving the problem of drug induced hospitalizations. Approximately 10–14% of all hospitalization (adults) in the U.S. are drug induced. While the total drug costs in the US are around $108 billion dollars, the estimated additional cost to the healthcare system of drug induced hospitalizations is an additional $40–50 billion dollars per year. The system of the present invention is designed to identify those patients at risk of drug induced hospitalization and produce interventions (in the form of alerts) to the prescribing physicians, in order to prevent the hospitalization.

The system of the present invention addresses the problem of drug induced hospitalization by combining the medical records database review with professional clinical review and judgment. Specifically, the process involves the (1) identification, (2) quantification, and (3) prioritization of patients at risk of drug induced hospitalizations. Identification involves passing the most current 60 days of drug and medical claims across the rules (criteria) engine to identify patients with conflicts.

Quantification involves scoring each conflicted patient, combining the contribution to risk of the conflict(s) and the additional underlying risk each specific patient has by virtue of age, sex, number of drugs, number of diseases, number of physicians, number of pharmacies, number of laboratory tests, number of laboratory rule (criteria) violations and exceptions. The individualized conflict patient scores are then prioritized, displaying lowest to highest score, plotted against the absolute risk of hospitalization. A small number (typically $95^{th}$ percentile and greater) of patients with the highest scores (greatest risk) then have the clinical profiles printed. Each conflicted patient profile (for those patients with the highest scores) is then individually reviewed by a clinical pharmacist and a specific determination is made as to which conflict or conflicts are "clinically significant" and if so, which physician or physicians should receive the alerts. Once the review is completed, the changes are incorporated in the computer run, and the profiles and alert letters are printed and mailed.

Prior art systems have used rules based on information derived solely from medical and pharmacy claims (diagnoses, procedures, and drugs). The additional of laboratory data and the associated logic greatly increases the specificity of the predictive nature of the system and increase the strength of the system and logic to identify those patients at risk of drug induced hospitalization.

BRIEF DESCRIPTION OF THE DRAWINGS

FIG. 10 is a block diagram illustrating the drug induced hospitalization risk review of the present invention that may supplement the review illustrated in FIG. 2.

DETAILED DESCRIPTION OF THE PRESENTLY PREFERRED EMBODIMENTS

The present invention relates to an apparatus for searching, analyzing and retrieving information from a database structure of health benefit records or medical records that includes one or more databases of pharmacy benefit claims (including outpatient drug claims), patient benefit claims (including inpatient and outpatient medical claims) and laboratory claims (including laboratory test results).

The Data Processing System

Figure 1:
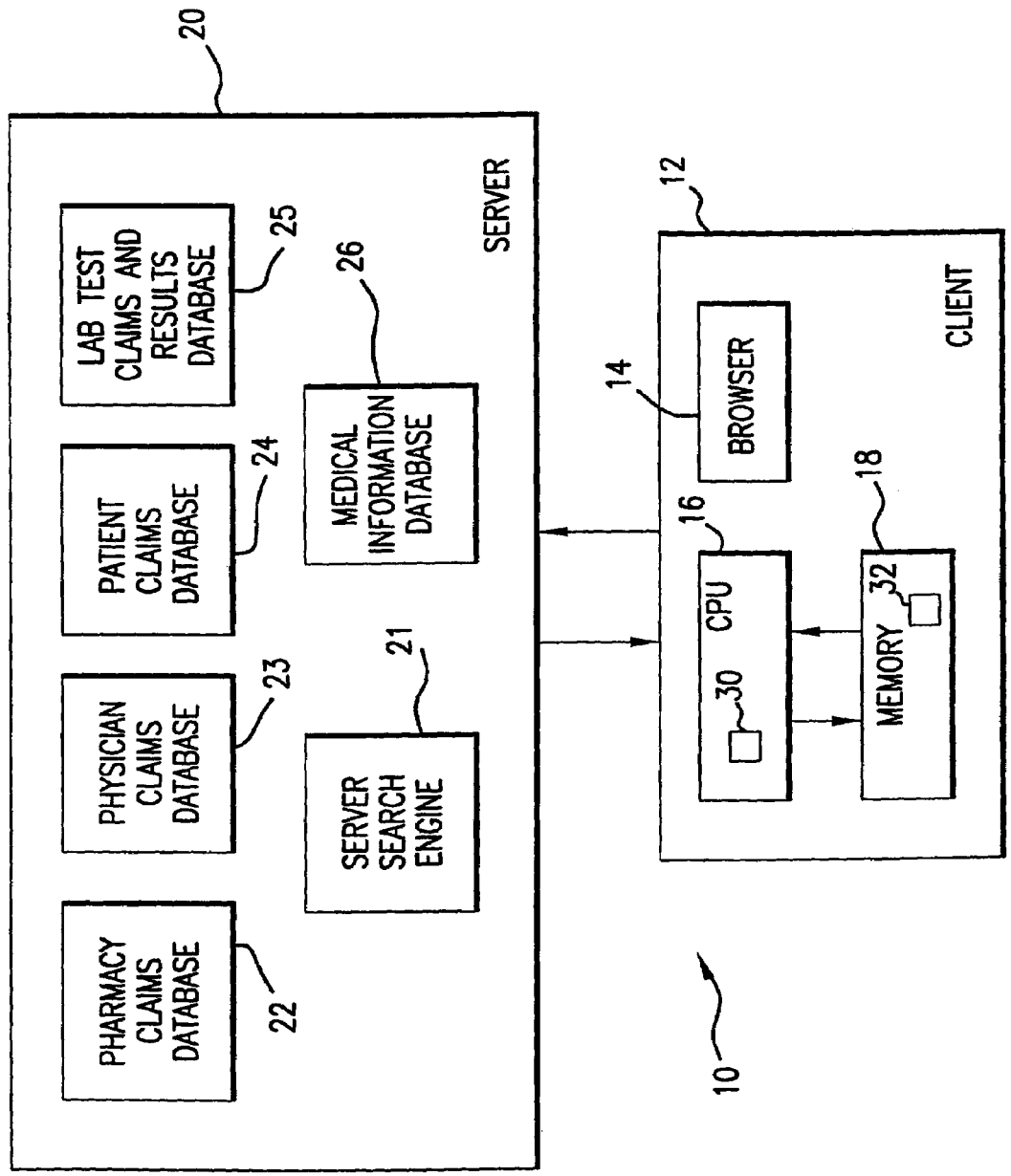
FIG. 1 is a block diagram illustrating one embodiment of the system of the present invention.

FIG. 1 illustrates a data processing system 10 for use with the present invention. Although illustrated in a client/server environment, the present invention may be used in various environments, such as a conventional personal computer or other hardware and software systems. The client system 12 includes a browser 14 as well as a central processing unit (CPU) 16 and a memory 18. The CPU can be any standard and commonly known central processing unit, and memory 18 can include magnetic ROM and RAM as known in the art. Memory unit 18 may be connected to the CPU and user from a remote location.

The server system 20 includes a server engine 21, or search engine, and various databases of medical records. Databases of medical records, or health benefit records utilized in one or more embodiments of the present invention include a pharmacy claims database 22 (including, for example, outpatient drug claims), a physician claims database 23 (including, for example, outpatient or inpatient claims submitted by a physician on behalf of a patient), a patient claims database 24 (including, for example, outpatient and inpatient benefit claims) and a laboratory test claims and test results database 25.

The server system 20 also includes a medical information database 26, which is a collection of criteria for implementation of the drug monitoring and regulation of the present system. The medical information database 26 includes criteria for the drug/drug interactions, drug/disease relationships and other reviews undertaken in the present invention, as described in detail below. The criteria for the medical information database 26 may be obtained from standard treatment guidelines, textbooks, compendial literature, journals, drug manufacturer guidelines or FDA requirements for particular drugs. The information database may be in the form of a look-up table, or similar structure, that provides output information based on the input of information obtained during the search of the other databases as acted upon by the rules of the logic structure of the system.

The system of the present invention can be operated by programs resident on the server side 20 or by operation of application programs 30, 32 that are executed by the CPU. Operator input is possible through a keyboard or other known input devices. Database records information can also be received from an external device or through an Internet connection or intranet connection, as known in the art. Each of the various databases may be stored or located in physically remote locations from one another or on a single client or single server system. Output is viewed through a standard graphical user interface or terminal or other known output devices.

Medical Records Inputs to the Database

The present invention utilizes this data processing system for user interface with the medical records databases. The medical records databases of the present invention are preferably formed from records relating to patient claims for health care benefits, but the present invention may be utilized with any number of types of medical record databases, as will be explained. In addition to medical records based on patient claims, the database may include records from related claims and information submitted by one or more treating physicians and other medical providers. The medical records database preferably includes conventional information regarding claims, such as patient identification by name and residence address (to also provide geographic data), patient age and sex, disease diagnosis, medical procedure identification and prescribed treatment, including drug or other therapy.

In the preferred embodiments of the present invention, the medical records database also includes records relating to regulation of drugs being provided to the patients. Such records may be provided by the doctor or patient in the form of a benefit claim or may be provided by a database of pharmaceutical claims, which would include records indicating the initiation of drug treatment and dose level of drug treatment. Discontinuation of drug treatment would also be indicated by such records by the lack of a record indicating continued treatment. For example, a regimen of 30 pills to be taken once daily would indicate discontinuation by the absence of a record indicating renewal of the prescription for an additional 30 day period.

Also included in the medical records database of the preferred embodiments of the present invention are laboratory test records. Preferably the laboratory test records include an identification of the specific tests performed by the laboratory and the results of those tests, as well as standard codes indicating patient identification, date of lab test, lab test code, lab test description and results, and an identification of the treatment provider who ordered the lab test. The relevance of the laboratory test result may be assessed in the context medical claims serving as indication of the presence or absence of particular diseases.

The above-described medical records, including patient, pharmaceutical and laboratory test records, are typically available in a conventional health benefits claims database. The system of the present invention makes use of those particular records in conjunction with a series of logic rules to provide predictive and informational results relating to presence of measured drug concentrations and indices of drug effectiveness.

Data Structure and Logic

Physicians and other health care workers create electronic records that represent the health records of their patients or other medically related records. The physicians and other workers may either manually express patient or other medically-related records in terms of codes and expressions that can be processed by the invention, or an interface may translate narrative patient records into codes and expressions that can be processed by the invention.

Similarly, pharmacies and other drug dispensing units create electronic records that represent the initiation or discontinuation of drug treatment for patients, as well as dosage levels of those treatments. Pathologists and other laboratory workers also create electronic records that represent the performance and outcomes of particular laboratory tests for patients. Those records may provide an indication of the concentration of a specific drug in a patient's blood, urine, spinal fluid, or other tissues or may indicate the presence of certain diseases. Other types of laboratory test results that are contemplated for possible use with the present invention include, without limitation, (1) hematology, (2) chemistry, (3) urinalysis, (4) bacteriology (culture and sensitivity), and (5) tissue/cytology.

The resulting sets of these electronic records comprise a database of records for use with the system of the present invention. The alphanumeric codes used in the patient/medical databases are the same as the alphanumeric codes of the corresponding concepts of the search engine and application software. For example, conventional ICD9CM diagnosis codes reported on health care claims and conventional NDC drug codes reported on health care claims may be used with the system of the present invention.

Any type of search engine known in the art may be used to review the relevant records, such as structured query logic (SQL) or similar systems. The specific software code for implementation of the system of the present invention may be devised and written by one skilled in the art based on the logic structure and data inputs described herein. The present invention relates more generally to the logic system for evaluation and review of the underlying data structure and medical records database than to the specific software code implementation of the system.

An example of the type of system used with the present invention would be a DEC Alpha server, with a VMS operating system, utilizing DEC RDB (Relational Database) as a database tool, utilizing Purveyor software for its internet interface. Internally, RDB uses SQL to support inquiries. Another example of the type of system that may be used with the present invention is an IBM RS6000 server with an AIX operating system running in a simultaneous multiple processing (SMP) environment, known as SP2, utilizing Oracle 8 as a database tool and Microstrategy as its inquiry tool. Other systems and configurations are possible.

The logic system will be described by reference to a series of examples illustrating the data elements and relevant logic factors. Criteria for drug dosage levels and interactions may be obtained from available treatment guidelines, medical textbooks, journals, pharmaceutical manufacturer guidelines and FDA requirements, as well as specific references detailing drug interaction guidelines. As previously noted, these criteria, and related information, are stored in a medical information database in the form of a look-up table, or other similar structure, and provide the criteria for decision making in the logic structure of the present invention. In each of the following examples, the various records databases are reviewed by the search engine for the identified patient information and the indicated output is provided to the system user or directly to a treatment provider.

Operation of System for Monitoring Regulation of Pharmaceuticals from Database of Medical Records In operation, the system of the present invention allows access to a database of medical records that preferably includes one or more of the following: records of patient claims, physician claims, pharmacy (or other drug dispensation) claims and laboratory test claims and test results. The system user initiates a system review that causes the records to be searched by the search engine and analyzed through a series of logic based rules. At various points in the search review, a comparison is made to data stored in a separate medical information database (such as a look-up table) that includes detailed information regarding drug/drug interactions and drug effectiveness. The invention contemplates update and revision of that separate information database as a result of information learned from the record review over a period of time.

Figure 2:
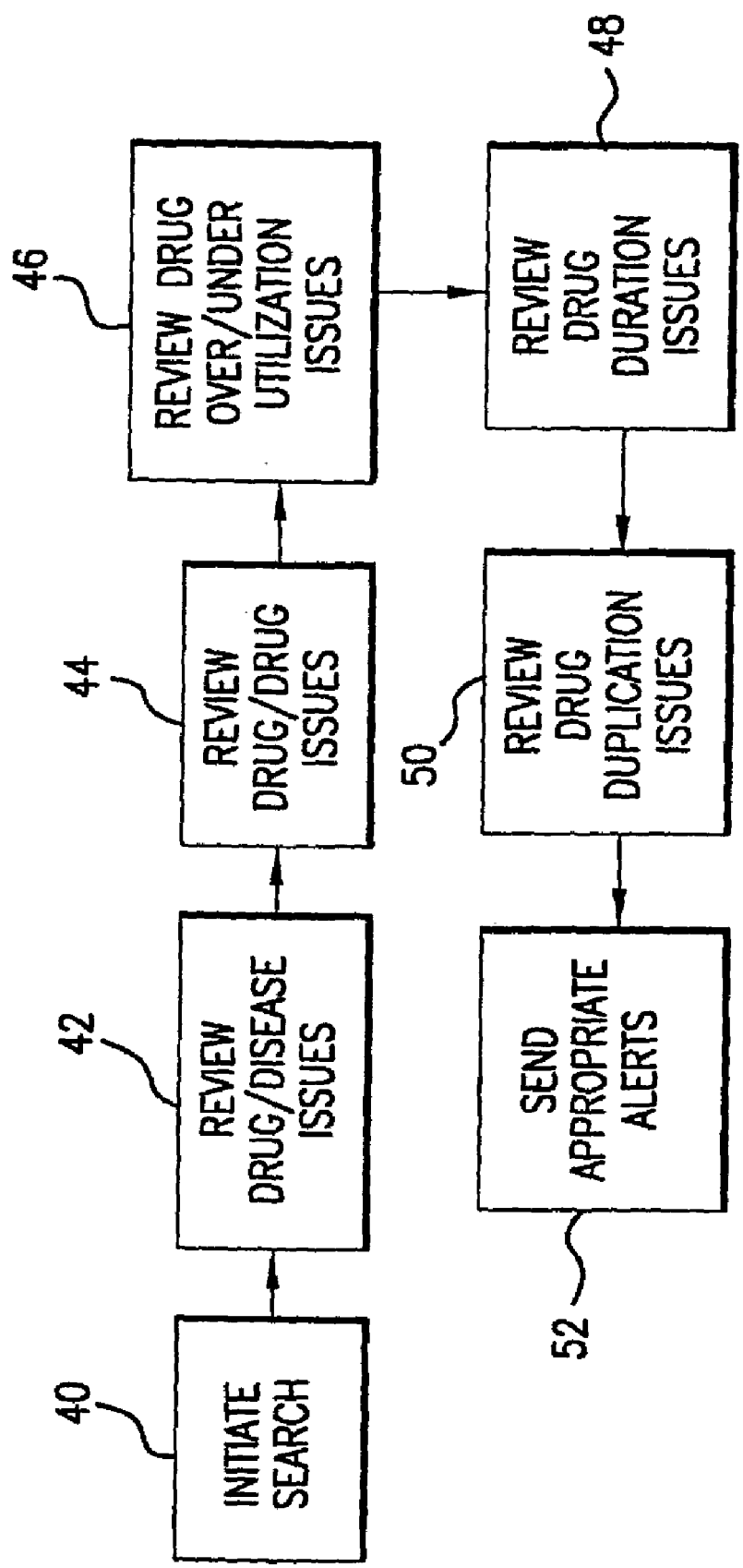
FIG. 2 is a block diagram illustrating the types of review of the databases undertaken by the system of the present invention.

FIG. 2 illustrates the different types of drug utilization review issues that are analyzed in one or more embodiments of the present invention. Upon initiation of a search 40, the system checks for drug/disease interactions 42. Certain types of drugs are contraindicated in the presence of certain diseases. For example, troglitazone [Rezulin] is contraindicated in the presence of liver disease. If the diagnosis of liver disease is not made, but a review of the laboratory test results indicates an abnormal liver function, the user (and eventually the treating physician) would be sent an alert warning that the drug should either not be prescribed or prescribed only with caution in such a patient. Similarly, Rezulin, which is used in the treatment of diabetes, requires a liver function test every month for the first 12 months of duration of usage. If a laboratory result of a liver function were not detected by the search engine, the system would send an alert to the user (and to the physician) indicating that a liver function test is necessary.

The system also checks for interactions 44 between different drugs. Certain drugs interact with each other in such a way as to render one or both of them either toxic (too high a level) or non-therapeutic (too low a level). An example would be a patient on theophylline for asthma, who was then given a macrolide antibiotic, such as erythromycin. The erythromycin interferes with the metabolism of the theophylline and can cause a toxic level. The system of the present invention, upon detection of prescription of both types of drugs, would send an alert that would suggest getting a lab test for the level of theophylline level and then suggest adjusting the dose of theophylline accordingly or suggest switching to another type of antibiotic that does not interfere with theophylline.

The system also reviews for over utilization and under utilization 46 of drug dosages. If the system detects over utilization (too high a dosage), which could lead to toxic level of the drug, an appropriate alert would suggest getting a lab test (to determine drug level). On the other hand, if the system detects under utilization (too low a dosage), or subtherapeutic levels of dosage, the alert would suggest getting a lab test (determine drug level), with recommendation of an appropriate adjustment in dosage level. The system also reviews drug duration issues 48, which relate to problems from use over an excessive time period. In such a situation, the alert might suggest a lab test (for measurement of drug level or measure of a certain metabolic function) if prolonged use of a drug was associated with certain types of toxicity, or increased risk, such as falling an hip fractures.

The system also reviews drug duplication issues 50. In such a case, the alert might suggest measuring metabolic function that would be affected by taking what would essentially be a "double" dose of a drug. In each of the various checks, appropriate alerts 52 are sent to the user, which may be the treating physician or a related health care provider.

Figure 3:
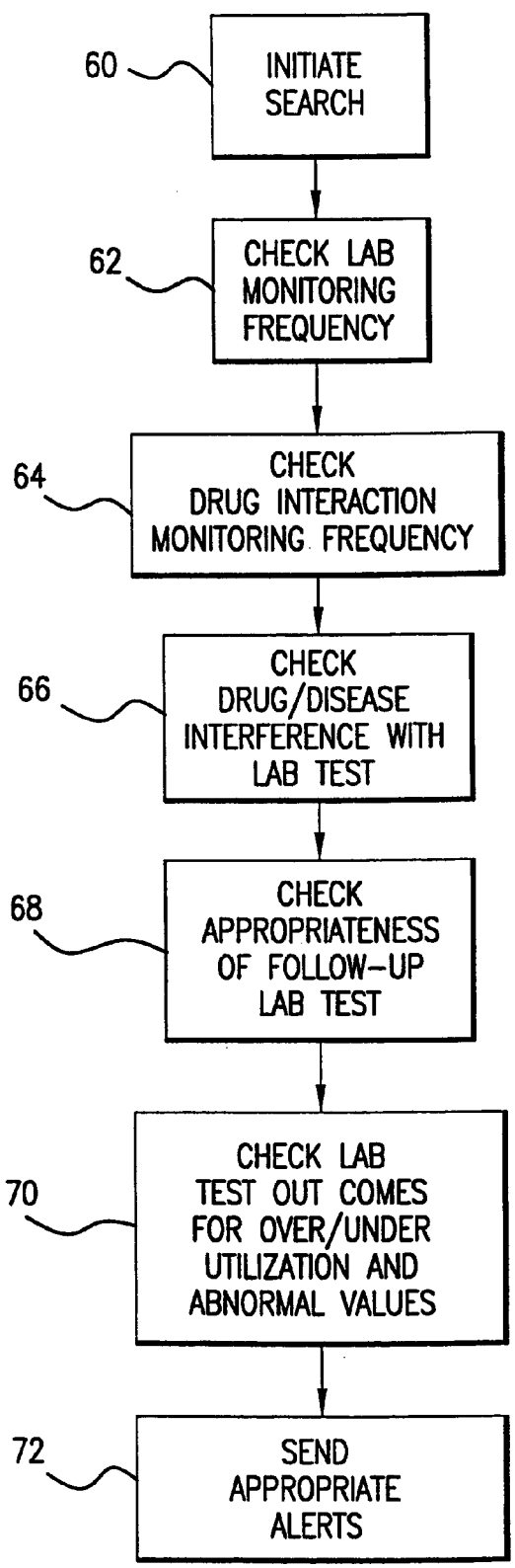
FIG. 3 is a block diagram illustrating in more detail the types of drug monitoring undertaken by the system of FIG. 2.
Figure 4:
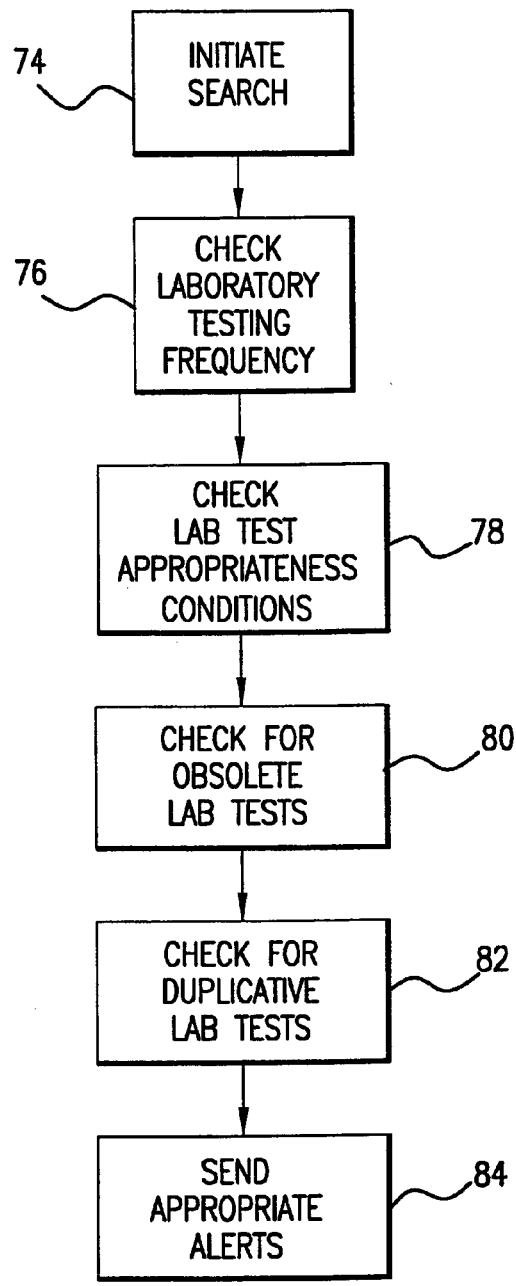
FIG. 4 is a block diagram illustrating in more detail the types of laboratory test monitoring undertaken by the system of FIG. 2.

FIGS. 3 and 4 include block diagrams that describe the various checks of FIG. 2 in more detail. As illustrated in FIG. 3, upon initiation of the search 60, a check is made for laboratory monitoring frequency 62. This check alerts users or other health care providers regarding the lack of appropriate laboratory monitoring required for a patient with a particular condition (disease or diagnosis) or taking a particular drug. An alert occurs if the appropriate lab test result code is not present in the designated time period.

A drug interaction monitoring check 64 alerts providers regarding the lack of appropriate laboratory monitoring required for a patient when an interacting drug is initiated or discontinued. An alert occurs if the appropriate lab test code is not present in the designated time period and a specific second drug (DRUG B) has been initiated or discontinued.

A drug/disease/lab interference check 66 alerts providers to the possible interference of a drug or disease with a laboratory test. Such interference is flagged when it would lead to test interpretation errors. An alert occurs if the lab test code is within X days of the last Rx or Dx code and is abnormal.

Lab test appropriateness check 68 alerts users to the need for a follow-up test when the result of the first lab test is abnormal. An alert occurs if the lab test no. 1 code is present in the current period and the result is abnormal and lab test no. 2 is not present.

Test outcomes check 70 alerts users to laboratory results that are associated with subtherapeutic dose (too low) or toxic dose (too high) or an abnormal value that indicates the presence of a side effect. An alert occurs if the lab test code is present in the current period and the result is abnormal.

For each of these checks, an appropriate alert 72 is sent to the user, if necessary.

FIG. 4 illustrates the various checks undertaken by the present system with regard to laboratory tests. Upon initiation of a search 74, a laboratory testing frequency check 76 provides a schedule of frequencies for certain laboratory tests, such as high cost lab tests, and alerts the user if the test frequency is above or below the recommended frequency. The recommended frequency may be dependent on the previous lab test result. For example a normal result may suggest a longer period of time between lab tests and an abnormal result may indicate the need for a shorter period of time until the next lab test. An alert occurs if the lab result is present or absent in the current period and the previous result was normal or abnormal.

A lab test appropriateness conditions check 78 alerts the user if a test is useless or invalid under certain conditions. For example, a lab test for ferritin may show invalid results if performed when the patient is an alcoholic because ferritin is released from a damaged liver. A direct bilirubin test is useless if total bilirubin is normal. An alert occurs if the lab test code is present in the current period and the previous result of another test was normal or abnormal or a conflicting condition is present in the current period.

An obsolete lab test check 80 identifies certain laboratory tests that are considered obsolete because they are unreliable and other preferred tests exist. An alert occurs if the lab test is present in the current period.

A duplicative lab test check 82 identifies certain laboratory tests that are considered duplicative because they measure the same functional area. An alert occurs if the lab test and the duplicative test are present in the current period.

For each of these checks, an appropriate alert 84 is sent to the user, if necessary.

Figure 5:
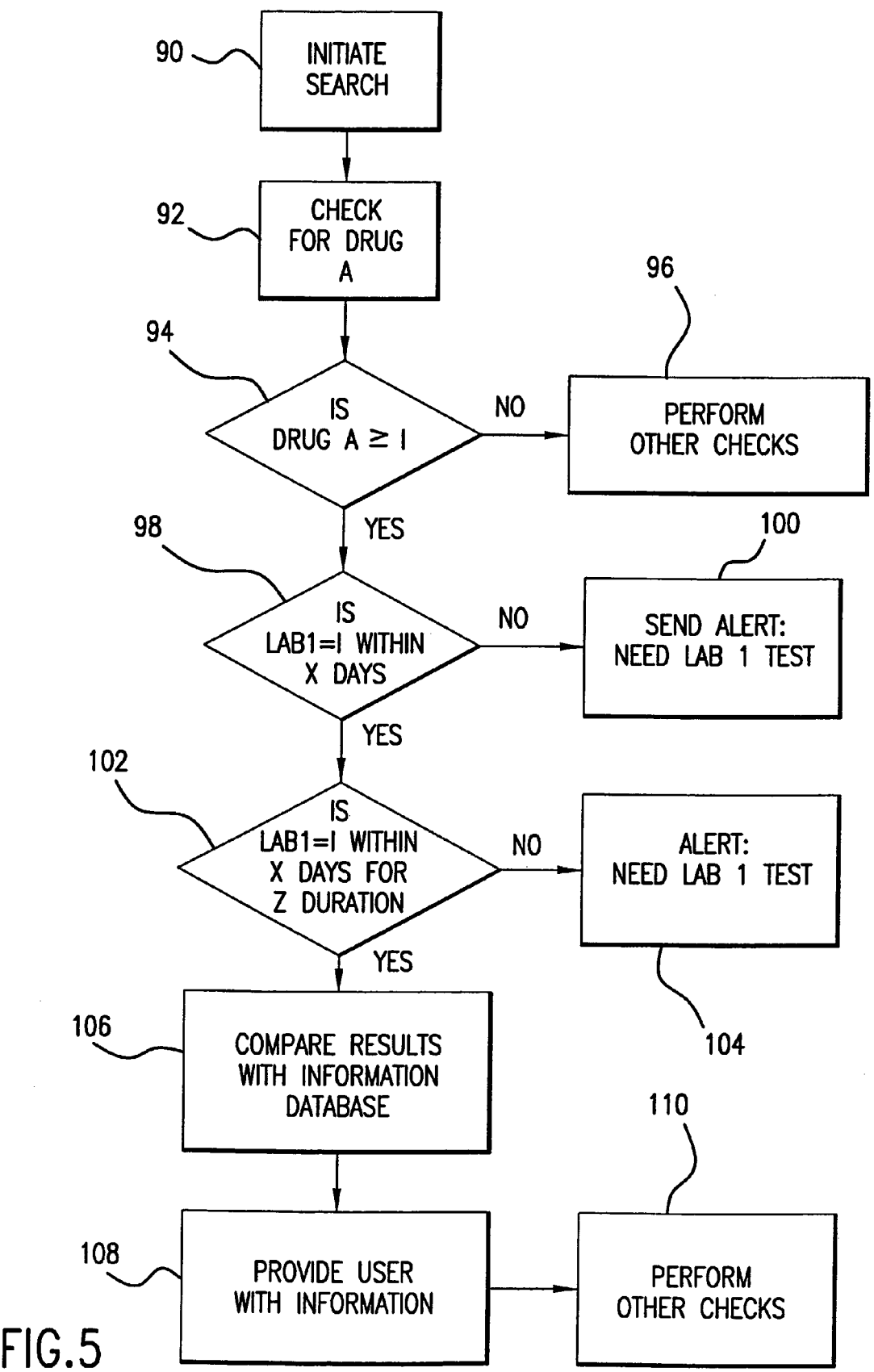
FIG. 5 is a flow diagram of a routine that monitors the frequency of laboratory tests for one drug.

FIGS. 5–9 illustrate example flow routines for implementation of the various checks for monitoring drug usage. As shown in FIG. 5, upon initiation of a search 90, the search engine searches 92 and identifies records having references to particular drugs, such as DRUG A, DRUG B, DRUG C, et seq. for each of the drugs referenced in the system. If DRUG A is identified in a particular record 94, then a series of evaluations relating to DRUG A are performed. If DRUG A is not identified in a particular record 94, then the search engine continues its search 96 with reference to DRUG B and DRUG C, until completion.

Upon identification 94 of a record with at least one dosage of DRUG A for PATIENT1, a search 98 is conducted for a laboratory report from LAB1 that indicates a test has been run relating to DRUG A within X days of the dosage report. Criteria for determination of the frequency of X days for such a test report is predetermined from treatment guidelines, textbooks, journals, manufacturer guidelines or FDA requirements, and is stored as part of the system or in the separate database of medical information, which can be accessed by the search engine during the search. This record check provides a confirmation that initiation of usage of DRUG A is being properly monitored with the correct laboratory test within the proper time period. Of course, many prescribed drugs do not require such lab testing upon initiation of usage and therefore the search would proceed accordingly without a search for laboratory test results.

Failure to locate such a test report causes an alert 100 to be sent to the user indicating that a laboratory test is needed within X days for proper monitoring of drug dosage. At this point, the search engine may also search for an indication of a disease or condition on the medical record of PATIENT1 corresponding to the prescription of DRUG A, and a separate comparison may be made of the database information with regard to effectiveness of use of DRUG A for treatment of the diagnosed disease or condition, with relevant information provided to the user as an output.

Positive identification of a test report from LAB1 within X days causes the search engine to then conduct a search 102 for confirmation that the subject test is repeatedly performed at LAB1 within a period of every X days for a duration period of Z days. Criteria for determination of the duration of Z days for performance of the required test is again predetermined from treatment guidelines, textbooks, journals, manufacturer guidelines or FDA requirements, and is stored as part of the database system or in the separate database of drug information, which can be accessed by the search engine during the search. This record check provides a confirmation that maintenance treatment with DRUG A is being properly monitored with the correct laboratory tests being repeatedly conducted within the proper time durations.

Failure to locate such a test report from LAB1 causes an alert 104 to be sent to the user indicating that a laboratory test is necessary. Positive identification of such a test report avoids the need for activation of any alert and the search engine proceeds accordingly. Positive identification of a test report may also cause a comparison 106 of the results of the test report with information in the database file for evaluation of the test results. The user may then be provided with information 108 about the results of the comparison. The search engine then proceeds with the other checks 110 described herein.

Figure 9:
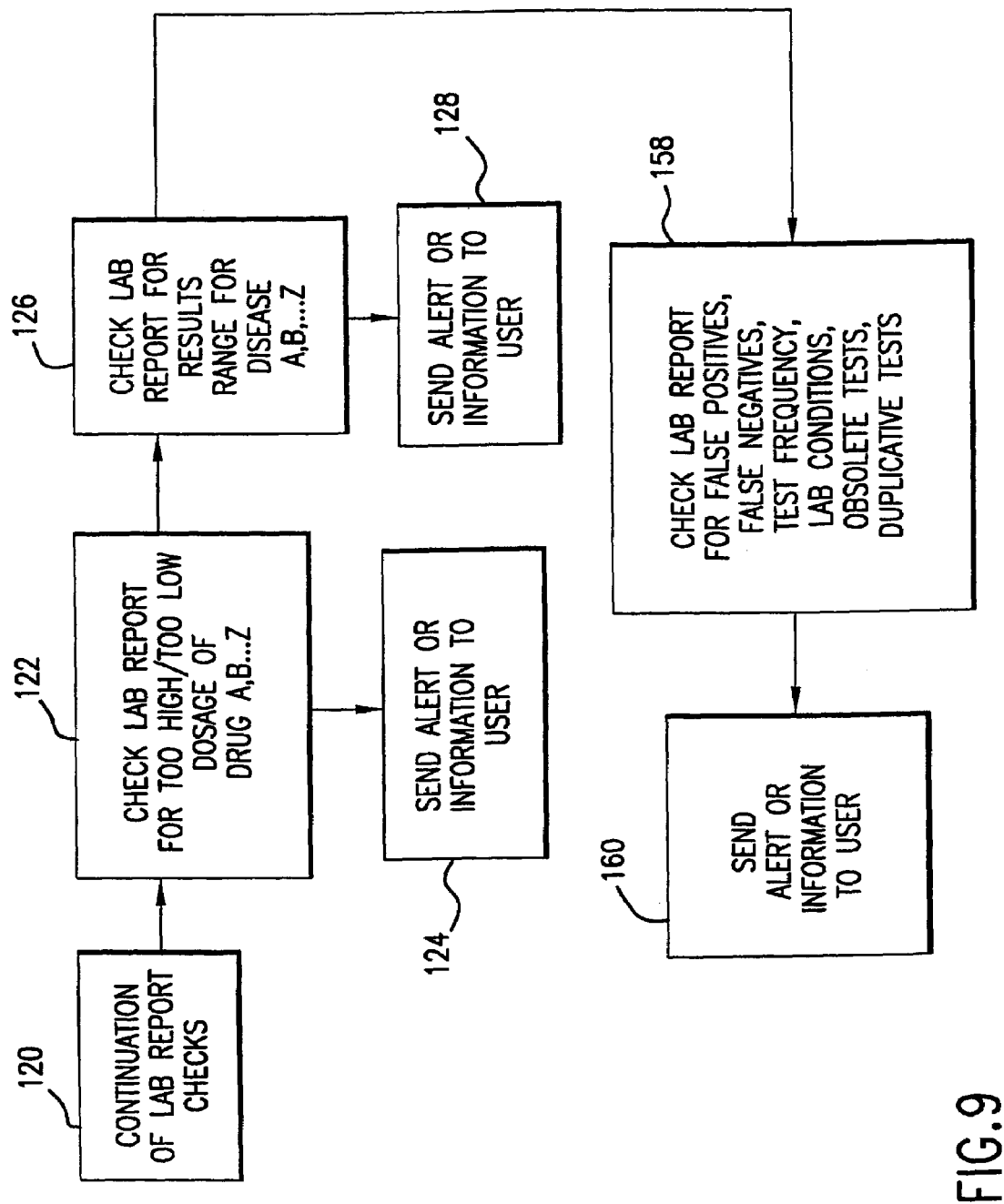
FIG. 9 is a block diagram illustrating additional checks performed by one embodiment of the system of the present invention.

Having completed the search routine for positive identification of prescription of at least one dosage of DRUG A, as shown in FIG. 9, the search engine continues the lab report checks 120 and conducts a search 122 for a medical record, preferably in the form of a prescription record, that indicates a change in dosage of DRUG A. Positive identification of such a record causes an evaluation of whether the change in dosage is greater than 50% of the previous dosage and another search for a laboratory record indicating that a test has been run relating to use of DRUG A within Y days after the increase in dosage.

Failure to locate such a test report causes an alert 124 to be sent to the user indicating the need for such a test. Positive identification of such a test report causes the search engine to provide a comparison of the LAB1 test results with information in the reference database with regard to dosage level effectiveness of DRUG A to treat the diagnosis or condition indicated for PATIENT1 on the medical record. This record check provides a monitoring of the change in dosage of a particular drug and can allow intervention with the treatment provider with regard to dosage effectiveness levels. In either case, an alert or other information 124 may be sent to the user.

Having completed the search routine for increased dosage level of DRUG A, the search engine performs a search 126 for records indicating the diagnosis or condition (DISEASE A) that has been indicated for PATIENT1 who is being prescribed DRUG A. As noted above, the information regarding diagnosis or condition may be used in conjunction with the other evaluation comparison. The system contemplates that the identification of diagnosis or condition will also be monitored with regard to whether particular laboratory tests are necessary or recommended in the treatment of such a condition.

Accordingly, upon identification of DISEASE A with PATIENT1, the search engine looks for a laboratory test report or test reports from LAB1 within X days during a duration of Z days after the first diagnosis of DISEASE A. Failure to positively identify such a lab report causes an alert 128 to be sent to the user. Identification of a test report causes a comparison of the test report results with the information database with regard to DISEASE A. This record check provides monitoring of specific diseases or conditions for necessary or preferred laboratory tests.

Figure 6:
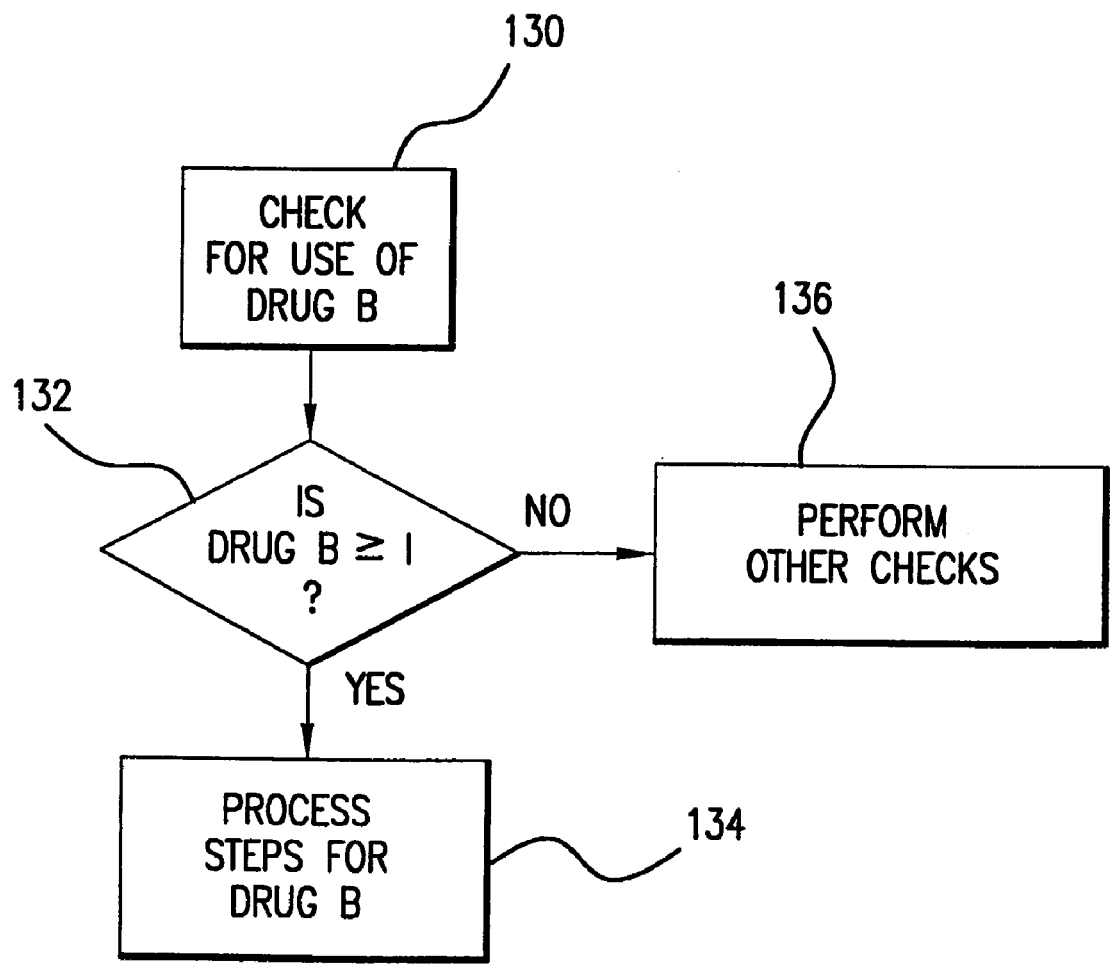
FIG. 6 is a flow diagram of a routine that monitors the frequency of laboratory tests for a second drug using the routine of FIG. 5.

Having completed the search routine for DISEASE A, the search engine continues with checks 130 for use of DRUG B by initiation of a search 132 for records for use of DRUG B. This routine is illustrated in FIG. 6. Upon finding a record indicating use of DRUG B, the search engine continues to perform the various checks 134 with regard to DRUG B. Failure to find a record for DRUG B causes the search engine to continue with its other checks 136.

Figure 7:
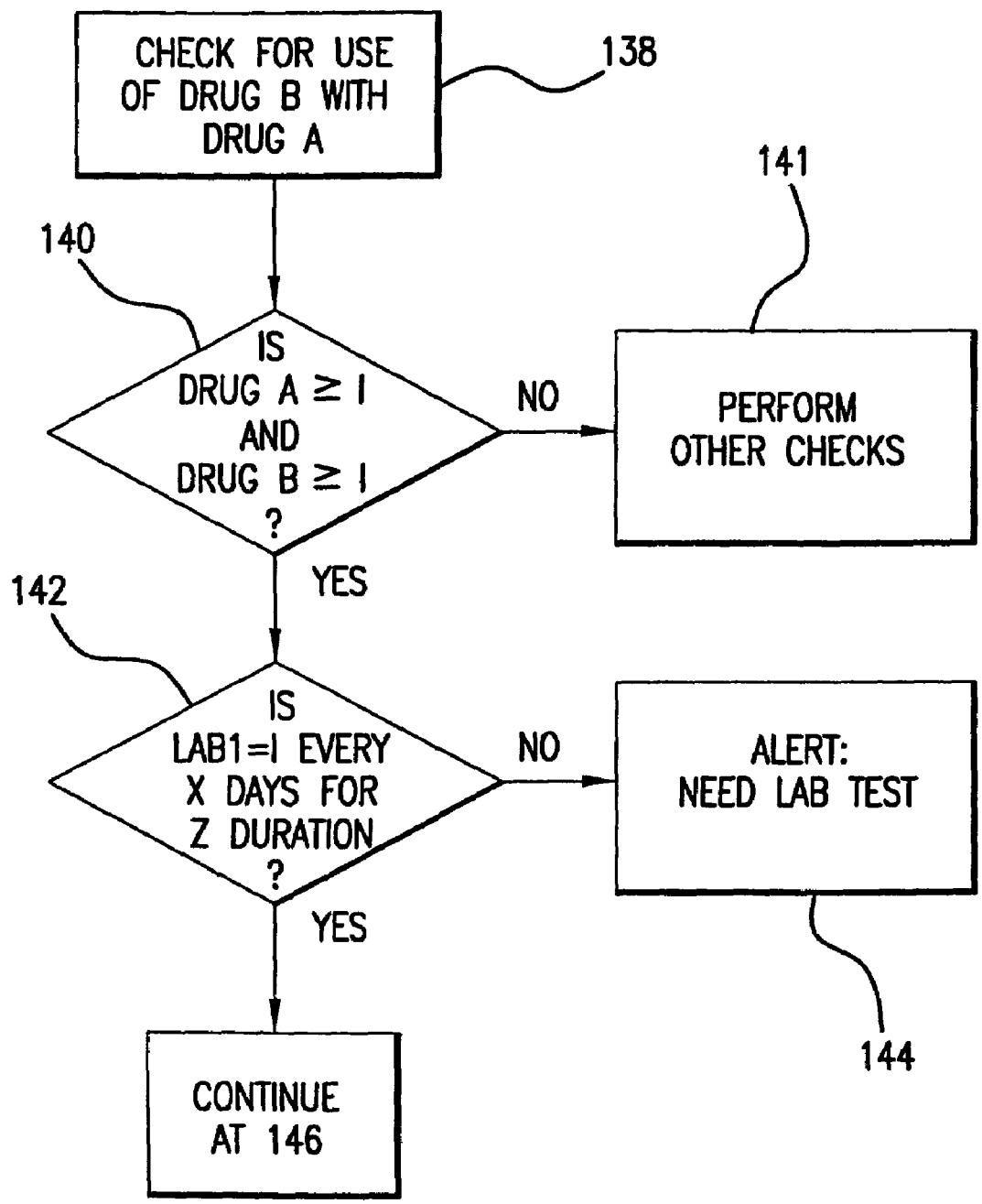
FIG. 7 is a first portion of a flow diagram of a routine that monitors the interaction of two drugs.
Figure 8:
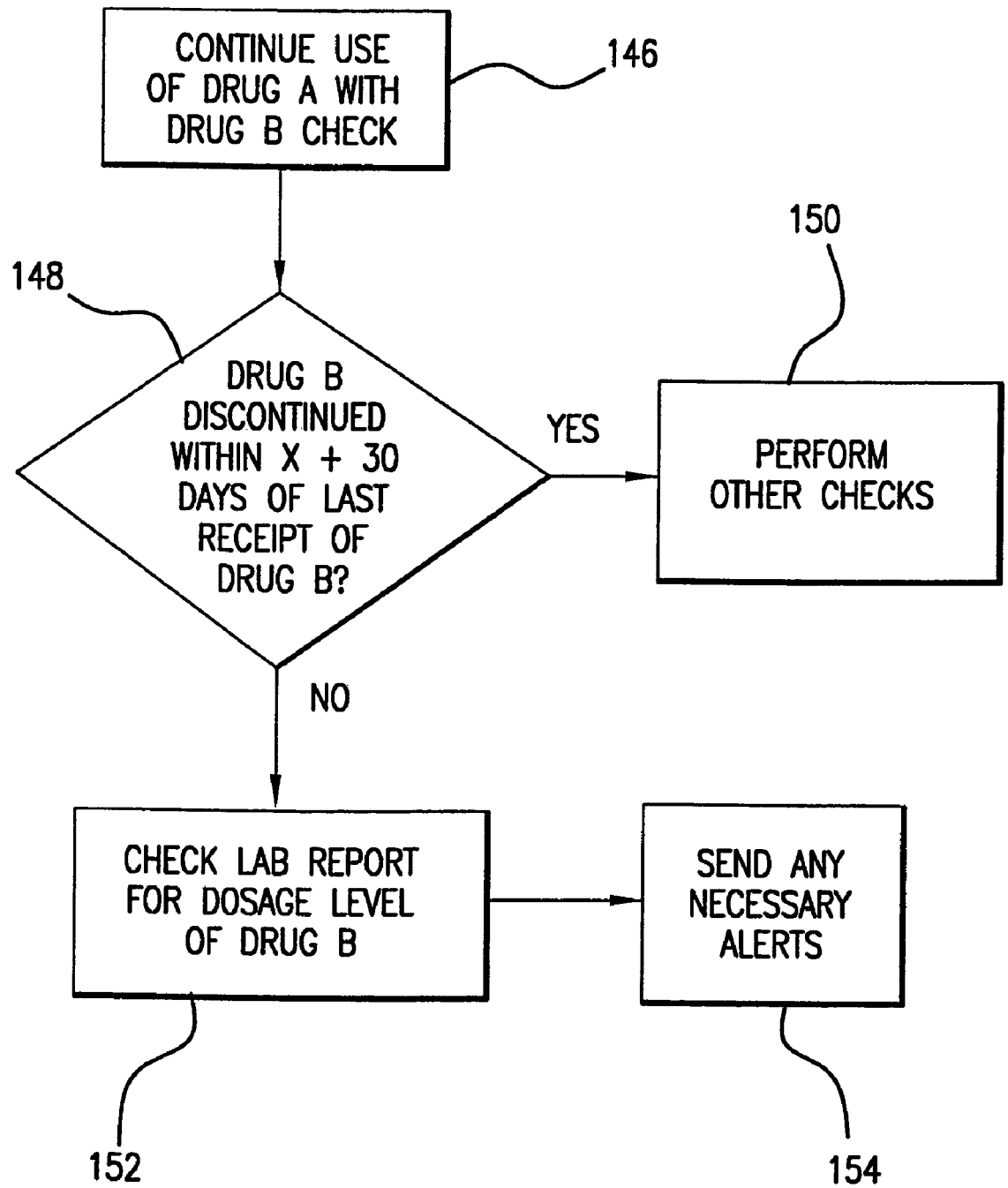
FIG. 8 is a second portion of the flow diagram of FIG. 7 of a routine that monitors the interaction of two drugs.

As illustrated in FIG. 7, the search engine then conducts a search 138 for a record 140 indicating initiation of use of DRUG B in PATIENT1 in combination with DRUG A. Failure to find such a record prompts the engine to continue to perform other checks 141, which may include checks for use of DRUG C, DRUG D, et seq. Positive identification of use of DRUG B in PATIENT1, along with use of DRUG A, causes monitoring 142 for a report from LAB1 every X days for a duration of Z days. Failure to positively identify such a lab report causes an alert 144 to be sent to the user. Positive identification of use of DRUG B in PATIENT1, along with use of DRUG A, also causes a review of the information database for an indication of drug/drug interactions with an alert sent to the user. Positive identification of a test report from LAB1 may also cause comparison of the test report results with the information database with regard to DISEASE A and provide information to the user on effectiveness of DRUG A and/or DRUG B with regard to DISEASE A. This record check provides a monitoring of drug interaction upon initiation of a second drug therapy.

Positive identification of initiation of usage of DRUG B causes the search engine to continue its review 146 of use of DRUG A with DRUG B and conduct a search 148 for records indicating discontinuation of usage of DRUG B. Such a search can be conducted by searching for the absence of records indicating renewal of a prescription for DRUG B within X+30 days after the last receipt of DRUG B. Positive identification of discontinuance of usage of DRUG B causes the search engine to proceed with other checks 150. Discontinuation may also be monitored through a review of lab reports from LAB1 for presence/absence of DRUG B every X days for a duration of Z days. Failure to find discontinuation of DRUG B causes a search 152 for a lab report to confirm the dosage level of DRUG B. Any alert 154 or other necessary information can be sent to the user In this manner, the search engine undertakes a review of various drug regulation criteria. Search engine review 122 of test reports of LAB1 for indications that the test results show a subtherapeutic (too low) dose of DRUG A or a toxic (too high) does of DRUG A causes an appropriate alert 124 to be sent to the user. Similarly, search engine review 126 of test reports of LAB1 is made for indications that the test results are above or below the normal range for patients with well-controlled DISEASE A, or that normally positive values are negative or that normally negative values are positive 158; such a finding causes an appropriate alert 160 to be sent to the user that a reevaluation of the patient's condition or diagnosis is necessary. Such results also suggest a reevaluation of the test results or a second test (LAB2) be conducted.

Search engine review of test reports of LAB1 is also made for indications that the results are testing falsely positive or falsely negative or above or below normal results as a result of interference between DRUG A and/or DISEASE A with the results of LAB1. The search engine also reviews the test reports of LAB1 for indications that the frequency of testing is not great enough or that the testing is being conducted too frequently. The search engine also checks for inappropriate conditions in LAB1, such as the lab markers, or the use of obsolete tests or duplicative tests. Appropriate alerts are sent to the user in each of these situations.

FIG. 9 illustrates in block diagram form several of the checks undertaken by the search engine without providing the detailed flow diagram for each such check. The search engine functions described herein are not limited to the examples or specific checks described. Numerous additional checks and reviews may be performed that would be within the scope of the present invention. Specific routines are contemplated for specific drugs, specific diseases, specific lab tests, and their interrelationships. Additionally, the present invention is not limited to any particular order for performance of the checks or any particular minimum or maximum number of checks. Further illustrations of the operation of the system of the present invention will be described by reference to specific examples.

EXAMPLES OF LOGIC STRUCTURE IMPLEMENTATION

Example I

Monitor Drug Initiation

Database search indicates that PATIENT1 has been prescribed DRUG A, i.e., (DRUG A>1). Detection of initiation of DRUG A causes monitoring for a report from LAB1 within X days after initiation of DRUG A for duration period of Z days. An alert is provided to the user if LAB1 indicates that no test has been run during the current period after initiation (i.e., within X days of Z duration). Monitoring of lab testing after initiation of treatment with DRUG A provides information regarding level of DRUG A in patient and effectiveness of DRUG A as treatment.

Examples of such a search routine would include: (1) initiation of amiodarone (DRUG A) requires monitoring for a lab test for thyroid stimulating hormone (TSH) every 180 days; (2) initiation of lovastatin (DRUG A) requires monitoring for a liver function lab test (LFT) every 6 weeks for 2 such periods, or 12 weeks total; (3) initiation of metformin (DRUG A) requires monitoring for a lab test for creatinine every 360 days; and, (4) initiation of thyroxine (DRUG A) requires monitoring for a lab test for TSH every 180 days.

Example II

Monitor Drug Frequency

Database search indicates that PATIENT1 has been provided two treatment phases of DRUG A (DRUG A>2). Detection of start of second treatment phase of DRUG A causes monitoring for report from LAB1 every X days for duration period of Z days. An alert is provided to the user if LAB1 indicates that it has not run at least one test during each period of X days for duration period of Z days, or an alert is provided to the user about the effectiveness of DRUG A for a second treatment phase for the disease indicated in the record. Monitoring of lab information regarding further treatment phases provides information about effectiveness of DRUG A as a treatment.

Examples of such a search routine would include: (1) maintenance treatment with amiodarone (DRUG A) requires monitoring for a liver function lab test (LFT) every 180 days; (2) maintenance treatment with simvastatin (DRUG A) requires monitoring for a liver function lab test (LFT) every 180 days; (3) maintenance treatment with colchicine (DRUG A) requires monitoring for lab test for complete blood count (CBC) every 180 days; and, (4) maintenance treatment with isotretinoin (DRUG A) requires monitoring for an HCG pregnancy lab test every 30 days.

Example III

Monitor Drug Dosage Changes

Database search indicates that PATIENT1 has been provided with a change in dosage level of greater than 50% of the previous dose of DRUG A ((DRUG A>2) AND (DOSE (NEW)>DOSE(PREV)×1.5). Detection of change in dosage level of DRUG A causes monitoring for report from LAB1 every X days for duration period of Z days. An alert is provided to the user if LAB1 indicates that it has not run at least one test during the period of X days for duration period of Z days, or an alert is provided about the level of dosage of DRUG A in the patient and the effectiveness of particular dosage levels of DRUG A for the treatment of the indicated disease.

Examples of such a search routine would include: (1) changing dosage of theophylline (DRUG A) requires monitoring for lab test for theophylline blood level after 5 half lives (t½ 3 to 15 hours); (2) changing dosage of digoxin (DRUG A) requires monitoring for lab test for digoxin blood level after 5 half lives lives (t½ 30 to 40 hours); (3) changing dosage level of phenytoin (DRUG A) requires monitoring for lab test for phenytoin blood level after 5 half lives lives (t½ 6 to 24 hours); and, (4) changing dosage level of lithium (DRUG A) requires monitoring for lab test for lithium blood level every 7 days for a total of 21 days.

Example IV

Monitoring of Disease

Database search indicates that PATIENT1 has DISEASE A (DISEASE(A)>1). Detection of presence of DISEASE A causes monitoring for report from LAB1 within X days after first indication of DISEASE A for duration period of Z days. An alert is provided to the user if such a report is not found or an alert is provided about the effectiveness of particular drugs or the need for particular tests from the laboratory.

Examples of such a search routine would include: (1) patient with diabetes (DISEASE A) requires monitoring for lab test for hemoglobin A1C (Hgb A1C) every 180 days; (2) patient with hypertension (DISEASE A) requires monitoring for lab test for creatinine every 365 days; and, (3) patient with pregnancy condition (DISEASE A) requires monitoring for lab test for urine protein every 30 days.

Example V

Drug Interaction

Database search indicates initiation of DRUG B in PATIENT1 with current usage of DRUG A (DRUG A>1, DRUG B>1). Detection of usage of DRUG B with DRUG A causes monitoring for report from LAB1 every X days for duration of Z days. An alert is provided to the user if such a report is not found or an alert is provided about possible interaction effects between DRUG A and DRUG B or the need for particular tests from the laboratory to monitor the levels of one or both drugs.

Examples of such a search routine would include: (1) initiation of troleandomycin (DRUG B) in patient taking theophylline (DRUG A) requires monitoring for lab test for theophylline level every 7 days; (2) initiation of furosemide (DRUG B) in patient taking a thiazide (DRUG A) requires monitoring for lab test for potassium every 180 days; and, (4) initiation of insulin (DRUG B) in patient taking a sulfonylurea (DRUG B) requires monitoring for a lab test for blood glucose level every 90 days.

Example VI

Drug Discontinuation

Database search indicates discontinuation of DRUG B in PATIENT1 who is currently using DRUG A (DRUG A>1, DRUG B=0). Detection of discontinuation of DRUG B by user of DRUG A causes monitoring for a report from LAB1 within X+30 days after the last use of DRUG B. An alert is provided to the user is such a report is not found or an alert is provided to the user about possible effects from the discontinuation of DRUG B.

Examples of such a search routine would include: (1) discontinuation of ticlopidine (DRUG B) in patient taking phenytoin (DRUG A) requires monitoring for lab test of phenytoin level; (2) discontinuation of troglitazone (DRUG B) in patient taking cyclosporine (DRUG A) requires monitoring for lab test of cyclosporine level; (3) discontinuation of diltiazem (DRUG B) in patient taking cyclosporine DRUG A) requires monitoring for lab test for cyclosporine level.

Example VII

Subtherapeutic Drug Dosage Level

Database search indicates that LAB1 result is below the lower range indicating a subtherapeutic dosage of DRUG A. Detection of usage of DRUG A causes monitoring for report from LAB1 within 30 days of first usage of DRUG A in order to monitor blood level. Detection of subtherapeutic dosage of DRUG A causes an alert to the user about the dosage level of DRUG A.

Examples of such a search routine would include: (1) lab test result for theophylline level is below the lower range indicating a subtherapeutic theophylline (DRUG A) dose or patient noncompliance and would send an alert to raise the dose level; (2) lab test result for digoxin level is below the lower range indicating a subtherapeutic digoxin (DRUG A) dose or patient noncompliance and would send an alert to raise the dose level; and, (3) lab test result for protime is below the lower range indicating a subtherapeutic warfarin (DRUG A) dose or patient noncompliance and would send an alert to raise the dose level.

Example VIII

Toxic Drug Dosage Level

Database search indicates that LAB1 result is above the normal range indicating a toxic dosage level of DRUG A. Detection of usage of DRUG A causes monitoring for report from LAB1 within 30 days of first usage of DRUG A in order to monitor blood level. Detection of toxic dosage of DRUG A causes an alert to the user about the dosage level of DRUG A.

Examples of such a search routine would include: (1) lab test result for phenytoin level is above the upper range indicating a toxic phenytoin (DRUG A) dose and would send an alert to lower the dose level; (2) lab test result for carbamazepine level is above the upper range indicating a toxic carbamazepine (DRUG A) dose and would send an alert to lower the dose level; (3) lab test result for lithium level is above the upper range indicating a toxic lithium (DRUG A) dose and would send an alert to lower the dose level.

Example IX

Disease (Condition) Reevaluation

Database search indicates that LAB1 result is below the lower range or above the upper range indicating a reevaluation of the diagnosis or condition as DISEASE A. Detection of diagnosis of DISEASE A causes monitoring for report from LAB1 within 30 days of diagnosis for lab markers indicating correct diagnosis of disease.

Examples of such a search routine would include: (1) lab test result for FEV1 level is below the lower range indicating a re-evaluation of this patient's asthma (DISEASE A) condition; (2) lab test result for potassium level is below the lower range indicating a re-evaluation of this patient's regimen treating congestive heart failure (DISEASE A) condition; (3) lab test result for lithium level is below the lower range indicating a re-evaluation of this patient's regimen treating mania (DISEASE A) condition; (4) lab test result for Hgb A1C level is above the upper range indicating a re-evaluation of this patient's diabetes (DISEASE A) condition; (5) lab test result for potassium level is above the upper range indicating a re-evaluation of this patient's regimen treating hypertension (DISEASE A) condition; and, (6) lab test result for TSH level is above the upper range indicating a re-evaluation of this patient's hypothyroidism (DISEASE A) condition.

Example X

Lab Marker Positives or Negatives

Database search indicates that LAB1 result is positive (when DISEASE A should indicate negative) or is negative (when DISEASE A should indicate positive) suggesting a reevaluation of the diagnosis or condition as DISEASE A. Detection of diagnosis of DISEASE A causes monitoring for report from LAB1 with lab markers indicating correct diagnosis of disease.

Examples of such a search routine would include: (1) lab test for Helicobacter pylon screening is positive indicating a re-evaluation of this patient's dyspepsia (DISEASE A) condition; (2) lab test for urine ketone is positive indicating a re-evaluation of this patient's diabetes (DISEASE A) condition; (3) lab test for basic drug screening is positive indicating a re-evaluation of this patient's anxiety (DISEASE A) condition; (4) lab test for anti-scleroderma-70 antibody is negative indicating a re-evaluation of this patient's scleroderma (DISEASE A) condition; (5) lab test for Bence Jones protein in urine is negative indicating a re-evaluation of this patient's myeloma (DISEASE A) condition; and, (6) lab test for anti-double stranded DNA antibodies is negative indicating a re-evaluation of this patient's systemic lupus erythematosus (DISEASE A) condition.

Example XI

Lab Results Appropriateness Above or Below Normal or Positive or Negative

Database search indicates that LAB1 result is above normal (when it should be below normal) or below normal (when it should be above normal) or positive (when it should be negative) or negative (when it should be positive). Alert is sent to user suggesting repeat test at LAB2 in light of such conditions. Alert is also sent to other users of LAB1 results for similar lab marker test.

Examples of such a search routine would include: (1) a second lab test for TSH (LAB2) is suggested since the lab test result for T4 (LAB1) is below normal; (2) a second lab test for absolute neutrophil count (LAB2) is suggested since the lab test result for WBC (LAB1) is below normal; (3) a second lab test for folic acid level (LAB2) is suggested since the lab test result for B12 level (LAB1) is below normal; (4) a second lab test for bilirubin (LAB2) is suggested since the lab test result for aspartate aminotransferase or lactic dehydrogenase (LDH) (LAB1) is above normal; (5) a second lab test for triglycerides (LAB2) is suggested since the lab test result for total cholesterol (LAB1) is above normal; (6) a second lab test for alkaline phosphatase (LAB2) is suggested since the lab test result for serum calcium (LAB1) is above normal; (7) a second lab test for CBC (LAB2) is suggested since lab test result for stool guiaic (LAB1) is positive; (8) a second lab test for urinanalysis (LAB2) is suggested since lab test result for urine protein (LAB1) is positive; (9) a second lab test seeking a follow-up throat culture (LAB2) is suggested since lab test result for rapid strep screen (LAB1) is positive; (10) a second lab test for CBC (LAB2) is suggested since lab test result for mono spot heterophile agglutination (LAB1) is negative; (11) a second lab test for vaginal ultrasound (LAB2) is suggested since lab test result for HCG pregnancy test (LAB1) is negative; and, (12) a second lab test for fluorescent treponema antibody absorbed (LAB2) is suggested since lab test result for VDRL (LAB1) is negative.

Example XII

False Positives, False Negatives or Other Result Interference

Database search indicates that DRUG A or DISEASE A interferes with LAB1 and may lead to false positive, false negative, falsely elevated, falsely decreased or other improper influences on the results. Alert is sent to user suggesting alternative test or other mechanism to minimize or eliminate the influence of DRUG A and/or DISEASE A on the results at LAB1.

Examples of such a search routine would include: (1) acetazolamide (DRUG A) interferes with lab test for urine protein (LAB1) and may lead to false positive results; (2) aminosalicylic acid (PAS) (DRUG A) interferes with lab test for urine glucose (LAB1) and may lead to false positive results; (3) Metformin (DRUG A) interferes with lab test for urine ketone (LAB1) and may lead to false positive results; (4) levodopa (DRUG A) interferes with lab test for urine glucose (LAB1) and may lead to false negative results; (5) vitamin C (high doses) (DRUG A) interferes with lab test for stool guiaic (LAB1) and may lead to false negative results; (6) ectopic pregnancy condition (DISEASE A) interferes with lab test for HCG pregnancy test (LAB1) and may lead to false negative results; (7) penicillamine (DRUG A) interferes with lab test for ESR erythrocyte sedimentation rate (LAB1) and may lead to falsely elevated results; (8) chlorpromazine (DRUG A) interferes with lab test for positive Direct Coombs' test (LAB1) and may lead to falsely elevated results; (9) griseofulvin (DRUG A) interferes with lab test for antinuclear antibodies (LAB1) and may lead to falsely elevated results; (10) quinine (DRUG A) interferes with lab test for ESR (LAB1) and may lead to falsely decreased results; (11) meprobamate (DRUG A) interferes with lab test for urine 17-ketosteroid (LAB1) and may lead to falsely decreased results; (12) imipramine (DRUG A) interferes with lab test for urine 5-HIAA (LAB1) and may lead to falsely decreased results; (13) oral contraceptives (DRUG A) interferes with lab test for glucose tolerance (LAB1) and may influence results; (14) cimetidine (DRUG A) interferes with lab test for serum creatinine (LAB1) and may influence results; and (15) clofibrate (DRUG A) interferes with lab test for serum triglycerides (LAB1) and may influence results.

Example XIII

Frequency Of Testing

Database search indicates normal or abnormal results obtained at LAB1. Alert sent to user that abnormal result indicates that LAB1 test should be performed again or every X days. Alert sent to user that normal result indicates that LAB1 test should be performed no more than every X days.

Example XIV

Inappropriate Conditions

Database search indicates that use of LAB1 results in patients with DISEASE A is not valid. Alert sent to user to modify conditions at LAB1 or use LAB2 for DISEASE A.

Example XV

Obsolete Tests

Database search indicates that LAB1 is using obsolete tests. Appropriate alert is sent to user.

Example XVI

Duplicative Tests

Database search indicates that LAB1 and LAB2 measure the same functional area and are considered duplicative. Appropriate alert is sent to user.

Drug Induced Hospitalization Risk Review

The present invention is also directed to solving the problem of drug induced hospitalizations. The system of the present invention is designed to identify those patients at risk of drug induced hospitalization and produce interventions (in the form of alerts) to the prescribing physicians, in order to prevent the hospitalization.

The system of the present invention addresses the problem of drug induced hospitalization by combining the medical records database review with professional clinical review and judgment. Specifically, the process involves the (1) identification, (2) quantification, and (3) prioritization of patients at risk of drug induced hospitalizations. This supplemental drug induced hospitalization risk review is illustrated in FIG. 10.

Identification 170 involves passing the most current 60 days of drug and medical claims across the rules (criteria) engine to identify patients with conflicts. An attempt is then made to quantify the risk of hospitalization by determining using a statistical analysis that addresses (1) the absolute risk of admission (the percent likelihood of being admitted for hospitalization) by consideration of the ratio of the number of hospitalized patients with conflicts to the total number of patients with conflicts, and (2) the relative risk of hospitalization (the odds of being admitted for hospitalization because of a particular conflict) by consideration of the ratio of the number of patients with a particular conflict that are hospitalized to the number of patients with the particular conflict that are not hospitalized.

Quantification 172 involves scoring each conflicted patient, combining the contribution to risk of the conflict(s) and the additional underlying risk each specific patient has by virtue of age, sex, number of drugs, number of diseases, number of physicians, number of pharmacies, number of laboratory tests, number of laboratory tests rule (criteria) violations/exceptions. The individualized conflict patient scores are then prioritized 174, displaying lowest to highest score, plotted against the absolute risk of hospitalization. A small number (typically those $95^{th}$ percentile and greater) of patients with the highest scores (greatest risk) then have the clinical profiles printed. Any of a number of types of statistical analysis techniques can be applied to determine the quantification of the risk of hospitalization.

Each conflicted patient profile (those with the highest scores) is then individually reviewed by a clinical pharmacist and a specific determination 176 is made as to which conflict or conflicts are "clinically significant" and if so, which physician or physicians should receive the alerts. Once the review is completed, the changes are incorporated in the computer run, and the profiles and alert letters are printed and sent 178 to the appropriate provider.

Improved Management From System Usage

The system of the present invention therefore provides various alerts to treatment providers that will allow opportunities for improved management of patients. In the preferred embodiments of the present system, alerts are provided to the users for false positive or false negative results caused by the presence of a confounding drug or disease condition. Alerts are provided to users if a lab value is not in the normal range and the patient's disease is not improving or if potential side effects are developing. Lab results in the normal range will indicate positive outcomes.

Alerts are also provided to users to direct attention to the lack of appropriate monitoring when required for a patient with a specific condition or particular drug. When patients are initially placed on a therapy, they should be monitored every X days for Z duration. Alerts are provided to users to monitor for drug levels or lab values if the initiation or discontinuation of a DRUG Affects the levels of another drug. Alerts are also provided if a lab value is not in the therapeutic range and will indicate if the patient's drug level is toxic or ineffective.

Those skilled in the art to which the invention pertains may make modifications and other embodiments employing the principles of this invention without departing from its spirit or essential characteristics, particularly upon considering the foregoing teachings. The described embodiments are to be considered in all respects only as illustrative and not restrictive and the scope of the invention is, therefore, indicated by the appended claims rather than by the foregoing description. Consequently, while the invention has been described with reference to particular embodiments, modifications of structure, sequence, materials and the like would be apparent to those skilled in the art, yet still fall within the scope of the invention.

What is claimed is:

1. A system useful for reducing the risk of a drug therapy related illness in a patient, the system comprising:
   at least one medical records database comprising: i) drug therapy records, said drug therapy records including an indication of patient identification and an indication of prescribed drug therapy associated with said patient identification, and ii) laboratory test result records, said laboratory test result records including an indication of patient identification and an indication of laboratory test results associated with said patient identification;

a medical information database, said medical information database including criteria pertaining to: i) interactions between a first drug and a second drag; ii) a relationship between the first drug and a first disease; and iii) administration of a laboratory test in connection with the administration of the first drug; and a search and determination engine for reviewing said laboratory test result records, said drug therapy records and said medical information database criteria, and for determining an output for reducing the risk of the drug therapy related illness in the patient using said laboratory test result records, said drug therapy records and the medical information database criteria by determining a drug interaction indicating initiation of the first drug in a patient with current usage of the second drug, including: (i) detecting the usage of the second drug concurrently with the first drug, (ii) monitoring for a laboratory report, (iii) generating an alert to the user of the system if such a report is not found, (iv) generating an alert to warn the user of the system about possible interaction effects between the first drug and the second drug; or (v) generating an alert to warn the user of the system of the need for particular tests from the laboratory to monitor the levels of the first and/or second drugs, wherein said system provides an output for the patient, to at least one of: (1) a treatment provider of the patient; or (2) a user of the system, wherein the output indicates the need for a laboratory test to be performed in connection with the care of said patient, and provides an alert to said treatment provider to prescribe said laboratory test, wherein said prescribing results in reducing the risk of a drug therapy related illness in said patient.

2. The system of claim 1 wherein said drug therapy records are physically remote from said laboratory test results.

3. The system of claim 1 wherein said medical records database comprises an integrated database.

4. The system of claim 1 wherein said medical records database further comprises patient health records, said patient health records including an indication of a disease diagnosis associated with said patient identification.

5. The system of claim 4 wherein said search engine reviews said patient health records and said medical information database criteria, and provides an output indicating the potential for a false positive or false negative laboratory result, thereby indicating the need for a reevaluation of a diagnosis of disease.

6. The system of claim 5 wherein the alert comprises a recommendation to perform a laboratory test, wherein the results of said laboratory test are useful in reducing the likelihood of a false positive output or a false negative output.

7. The system of claim 4 wherein said patient health records include inpatient and outpatient health benefit claims.

8. The system of claim 4 wherein said patient health records include records of physician claims made on behalf of patients.

9. The system of claim 1 wherein said drug therapy records include pharmaceutical benefit claims.

10. The system of claim 1 wherein said criteria in said medical information database comprises data pertaining to at least one of: (1) drug treatment guidelines, (2) textbooks, (3) journals, (4) pharmaceutical manufacturer guidelines and (5) FDA requirements.

11. The system of claim 1 wherein said medical information database is in the form of a look-up table.

12. The system of claim 1 wherein said absence of the laboratory test pertains to a need for a laboratory test pursuant to a change in a prescribed dosage level of the prescribed drug.

13. The system of claim 1 wherein said alert pertains to a diagnosis of a first disease type and monitoring laboratory test result records for a predetermined time.

14. The system of claim 1 wherein when the second drug comprises insulin, the first drug is in the sulfonylurea class, and the laboratory test referred to in the output pertains to the patient's blood glucose level.

15. The system of claim 1 wherein said alert indicates a need to increase or decrease the dosage level of a prescribed drug which has been prescribed for the patient.

16. The system of claim 1 wherein said search engine review further includes: detection of abnormal laboratory test results indicating the need for an additional laboratory test.

17. The system of claim 1 wherein said search engine review identifies conflicts between said prescribed drug therapy and said criteria for drug usage regulation, said conflicts being quantified by risk factors relating to risk of drug induced hospitalization.

18. The system of claim 17 wherein said risk factors include an assessment of factors relating to one or more of the group of: (1) patient age, (2) patient sex, (3) number of drugs prescribed to a patient, (4) number of physicians treating a patient, (5) number of pharmacies prescribing drugs to a patient, (6) number of laboratory tests, and (7) number of laboratory test triggering conflicts.

19. The system of claim 17 wherein said patients having said identified conflicts are prioritized based on risk of drug-induced hospitalization.

20. The system of claim 19 wherein said prioritized patients are further segregated by clinically significant risks of drug-induced hospitalization.

21. The system of claim 20 wherein at least one alert pertaining to clinically significant risks is sent to a treating physician as a result of said segregation by a clinical pharmacist.

22. The system of claim 21 wherein said at least one alert causes modification of at least one action of said treating physician.

23. A system for detecting a subtherapeutic drug dosage or a toxic drug dosages in a patient receiving drug therapy, said system comprising:

at least one medical records database comprising: i) drug therapy records, said drug therapy records including an indication of patient identification and an indication of prescribed drug therapy associated with said patient identification, and ii) laboratory test result records, said laboratory test result records including an indication of patient identification and an indication of laboratory test results associated with said patient identification;

a medical information database, said medical information database including criteria for drug usage regulation; and a search and determination engine receiving a user query and reviewing at least a portion of said laboratory test result records and at least a portion of at least one of said drug therapy records and said criteria for drug usage regulation, and determining an output for detecting a subtherapeutic drug dosage or a toxic drug dosages in a patient receiving drug therapy, wherein said laboratory test result records, said drug therapy records and said medical information database criteria are used for the determining of the output, wherein said system provides an output for the patient, wherein the output indicates at least one of:
  i) an alert suggesting that a laboratory tests be performed to detect a toxic dosage of a drug that is being administered to the patient; and
  ii) an alert suggesting that a laboratory tests be performed to detect a subtherapeutic dosage of a drug that is being administered to the patient.

24. A method for detecting a subtherapeutic drug dosage or a toxic drug dosages in a patient receiving drug therapy, said method comprising:
  providing at least one medical records database comprising: i) drug therapy records, said drug therapy records including an indication of patient identification and an indication of prescribed drug therapy associated with said patient identification, and ii) laboratory test result records, said laboratory test result records including an indication of patient identification and an indication of laboratory test results associated with said patient identification;
  providing a medical information database, said medical information database including data pertaining to interaction of a first prescribed drug and a second prescribed drug; and
  utilizing a search and determination engine to receive a user query and review at least a portion of said laboratory test result records, said drug therapy records and the data pertaining to interaction of a first prescribed drug and a second prescribed drug, and to determine an output for detecting a subtherapeutic drug dosage or a toxic drug dosage in a patient receiving drug therapy, wherein the laboratory test result records, the drug therapy records and the medical information database criteria are used for the determining of the output,
  wherein said method provides an output for the patient, to at least one of: (1) a treatment provider of the patient; or (2) a user of the system, said output indicating at least one of:
    i) an alert suggesting that a laboratory test be performed to detect a toxic dosage of a drug that is being administered to the patient; and
    ii) an alert suggesting that a laboratory test be performed to detect a subtherapeutic dosage of a drug that is being administered to the patient.

25. The method of claim 24, wherein the medical information database further includes data pertaining to drug and disease interactions.

26. The method of claim 24, wherein the output further includes an indication of a need for the patient to undergo a liver function test.

27. A computer-implemented and human-assisted method for identifying a risk of drug induced hospitalization, comprising:
  providing a medical information database comprising criteria pertaining to: i) at least one drug that is contraindicated in the presence of at least one disease; ii) at least one interaction between a first prescribed drug and a second prescribed drug, wherein the interaction renders one or both of the first and second drugs toxic or subtherapeutic; iii) criteria for overutilization of a prescribed drug; iv) criteria for underutilization of a prescribed drug; v) laboratory test result records, said laboratory test result records including an indication of patient identification and an indication of laboratory test results associated with the patient identification; and vi) criteria for use of a prescribed drug for an excessive time period;
  providing a plurality of drug therapy records comprising a patient identification and a patient prescribed drug therapy;
  comparing the drug therapy records and the medical information database to identify patients having at least one criteria as specified in the medical information database;
  quantifying the risk of drug induced hospitalization by utilizing: i) the criteria identified in said comparing step and ii) at least one patient attribute;
  identifying patients having a clinically significant risk, and
  providing a communication to a medical provider, indicating patients having a clinically significant risk and informing the medical provider of the clinically significant risk.

28. The method of claim 27 wherein the patient attributes comprise age, sex, number of prescribed drugs, number of diseases, number of physicians, number of pharmacies, and a number of laboratory tests.

29. The method of claim 27 wherein the communication is a written communication.

30. A system for identifying a risk of drug induced hospitalization, said system comprising:
  (I) a server system comprising:
  (1) a medical records database, wherein said medical records database comprises:
    i) a pharmaceutical claims database comprising data pertaining to drug treatment and drug dosage information for at least one patient;
    ii) a patient claims database comprising data comprising records from medical claims made on behalf of the patient, and information submitted by one or more treating physicians or other medical providers in connection with the patient;
    iii) a laboratory test claims results database comprising data pertaining to: laboratory tests performed for the patient, laboratory test results for the patient, a date of a laboratory test, a laboratory test description, and an identification of a treatment provider who ordered a laboratory test; and
    iv) a medical information database comprising criteria pertaining to: at least one interaction between a first prescribed drug and a second prescribed drug which renders one or both of the first and second drugs toxic or ineffective; an overutilization of a prescribed drug; an underutilization of a prescribed drug; a use of a prescribed drug for an excessive time period; an interaction between a drug and a disease; and a duplication of a prescribed drug, and
  (2) a server engine for comparing the medical information database and at least the patient claims database to identify a patient having at least one criteria as specified in the medical information database, and for determining an output for detecting the risk of drug induced hospitalization in a patient receiving drug therapy using said laboratory test result records, said drug therapy records and said medical information database criteria;
  said server system quantifying the risk of drug induced hospitalization for the patient by utilizing: i) the criteria identified by said server search engine and ii) at least one attribute of the patient, the at least one attribute comprising an age, a sex, a number of prescribed drugs, a number of diseases, a number of physicians, a number of pharmacies, and a number of laboratory test results, wherein the risk of drug induced hospitalization comprises:

an absolute risk of drug induced hospitalization, defined as a ratio of a number of hospitalized patients having criteria identified by said server search engine to a total number of patients having criteria identified by said server search engine; and a relative risk of drug induced hospitalization defined as a ratio of a number of patients having a particular criteria identified by said server search engine that are hospitalized to a total number of patients having a same particular criteria identified by said server search engine that are not hospitalized; said server system prioritizing the relative risk of drug induced hospitalization for the at least one patient by selecting a predetermined percentage of the at least one patient having the highest relative risk of drug induced hospitalization; and (II) a medical professional for reviewing medical data of the predetermined percentage of the patient having the highest relative risk of drug induced hospitalization to determine which of the at least one patient has clinically significant criteria identified by said server search engine, wherein said server system provides the output, suitable for delivery to a physician treating the patient, indicating that the patient has a clinically significant risk of drug induced hospitalization.

* * * * *